(12) United States Patent
Bullin et al.

(10) Patent No.: US 7,250,449 B2
(45) Date of Patent: Jul. 31, 2007

(54) HIGH TEMPERATURE HYDROCARBON CRACKING

(75) Inventors: Keith A. Bullin, Brazos County, TX (US); Joel G. Cantrell, Brazos County, TX (US)

(73) Assignee: Bryan Research & Engineering, Inc., Bryan, TX (US)

( * ) Notice: Subject to any disclaimer, the term of this patent is extended or adjusted under 35 U.S.C. 154(b) by 0 days.

(21) Appl. No.: 10/493,115

(22) PCT Filed: Oct. 18, 2002

(86) PCT No.: PCT/US02/33414

§ 371 (c)(1),
(2), (4) Date: Nov. 5, 2004

(87) PCT Pub. No.: WO03/033444

PCT Pub. Date: Apr. 24, 2003

(65) Prior Publication Data

US 2005/0065223 A1   Mar. 24, 2005

(51) Int. Cl.
*C07C 27/00* (2006.01)
*C07C 11/00* (2006.01)
*C07C 2/56* (2006.01)

(52) U.S. Cl. ............ 518/700; 518/705; 585/540; 585/541; 585/79

(58) Field of Classification Search ......... 518/700, 518/705; 585/540, 541, 709
See application file for complete search history.

(56) References Cited

U.S. PATENT DOCUMENTS

| | | | |
|---|---|---|---|
| 2,498,444 A | * | 2/1950 | Orr, Jr. ............... 585/541 |
| 3,156,733 A | | 11/1964 | Happel et al. |
| 3,389,189 A | | 6/1968 | Hirayama et al. |
| 5,131,993 A | | 7/1992 | Suib et al. |
| 5,277,773 A | | 1/1994 | Murphy |
| 6,130,260 A | | 10/2000 | Hall et al. |

* cited by examiner

*Primary Examiner*—J. Parsa
(74) *Attorney, Agent, or Firm*—Browning Bushman PC

(57) ABSTRACT

A process for converting natural gas to a hydrocarbon liquid wherein a stream of natural gas at a selected pressure is mixed with a hot gas stream which is at a temperature sufficient to affect a chemical reaction and form an intermediate product stream containing reactive hydrocarbons, the intermediate product stream being quenched and the quenched intermediate product stream being reacted in a catalytic liquification zone to produce a hydrocarbon liquid.

3 Claims, 2 Drawing Sheets

HIGH TEMPERATURE HYDROCARBON CRACKING

FIELD OF THE INVENTION

This invention pertains to the conversion of natural gas to liquid hydrocarbons.

BACKGROUND OF THE INVENTION

Natural gas often contains about 90 mole percent methane mixed with heavier alkanes. Alkanes of increasing carbon number are normally present in decreasing amounts. Carbon dioxide and other gases may be present.

Conversion of natural gas into hydrocarbon liquids has been a technological goal for many years. The goal has become even more important in recent years as more natural gas has been found in remote locations, where gas pipelines may not be economically justified. A significant portion of the world's reserves of natural gas occurs in such remote regions. While liquefied natural gas (LNG) and methanol projects have long attracted attention by making possible conversion of natural gas to a liquid, in recent years the advent of large scale projects based upon Fisher-Tropsch (F-T) technology have attracted more attention. A review of proposed and existing F-T projects along with a discussion of economics of the projects has recently been published (Oil and Gas J., Sep. 21 and Sep. 28, 1998). In this technology, natural gas is first converted to "syngas," which is a mixture of carbon monoxide and hydrogen, and the syngas is converted to liquid paraffinic and olefinic hydrocarbons of varying chain lengths. The F-T technology was developed for using coal as a feed stock, and only two plants now operate using natural gas as feedstock—in South Africa and in Malaysia. A study showed that for a plant producing 45,000 bbls/day (BPD) of liquids in a U.S. location in 1993, investment costs would have been about $38,000 per BPD production (Oil and Gas J., Sep. 28, 1998, p. 99). Improved designs are said to lower investment cost to the range of $30,000 per BPD for a 20,000 BPD facility. Such a plant would use about 180 MMSCFD of natural gas, 10 million GPD of raw water and 150 BPD of normal butane, and would produce excess steam, which could be used to produce 10 megawatts of electricity.

The conversion of methane to unsaturated hydrocarbons and hydrogen by subjecting the methane and other hydrocarbons in natural gas to high temperatures produced by electromagnetic radiation or electrical discharges has been extensively studied. U.S. Pat. No. 5,277,773 discloses a conversion process that subjects the methane plus hydrocarbons to microwave radiation so as to produce an electric discharge in an electromagnetic field. U.S. Pat. No. 5,131,993 discloses a method for cracking a hydrocarbon material in the presence of a microwave discharge plasma and a carrier gas, such as oxygen, hydrogen and nitrogen, and, generally, a catalyst. U.S. Pat. No. 3,389,189 is an example of patents relating to production of acetylene by an electric arc.

Methane pyrolysis to acetylene and hydrogen by rapid heating in a reaction zone and subsequent rapid quenching has also been extensively investigated. Subatmospheric pressures and specific ranges of velocities of hydrocarbon gases through the reaction zone are disclosed in U.S. Pat. No. 3,156,733. Heat is supplied by burning of hydrocarbons.

U.S. Pat. No. 6,130,260, incorporated herein by reference for all purposes, discloses a process for converting natural gas to a liquid wherein the natural gas is heated to a selected range of temperatures to convert a fraction thereof to reactive hydrocarbons, primarily acetylene, followed by reaction of the reactive hydrocarbons in the presence of an acidic catalyst to produce a liquid, predominantly aromatics and isoparaffins, product stream. The process is characterized by the fact that it is energy efficient, primarily self-sufficient, with the net result that all of the natural gas input is available to convert to liquids.

DESCRIPTION OF PREFERRED EMBODIMENTS

According to a preferred embodiment of the process of the present invention, natural gas is converted to a liquid hydrocarbon by providing a feed stream of natural gas at a pre-selected pressure, mixing the natural gas stream with a heated gas stream which is at a temperature sufficient to effect a chemical reaction to form an intermediate product stream containing reactive hydrocarbons. The intermediate product stream is quenched and subsequently reacted in a catalytic liquefaction zone to produce at least one hydrocarbon liquid, the hydrocarbon liquid being recovered, hydrocarbon gasses from the liquefaction zone being recycled to the feed stream.

Figure 1:
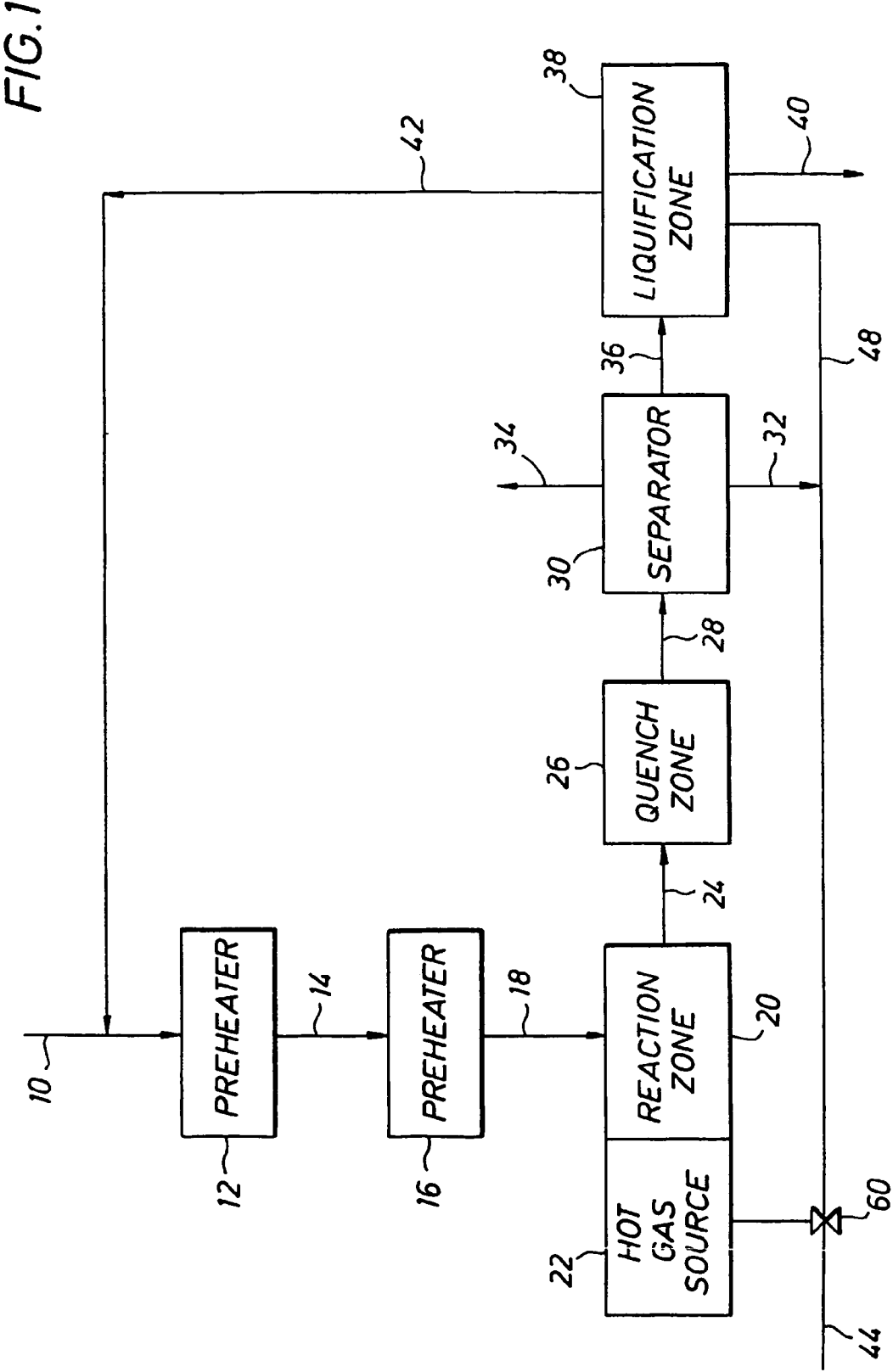
FIG. 1 is a schematic diagram of one embodiment of the process of the present invention.
Figure 2:
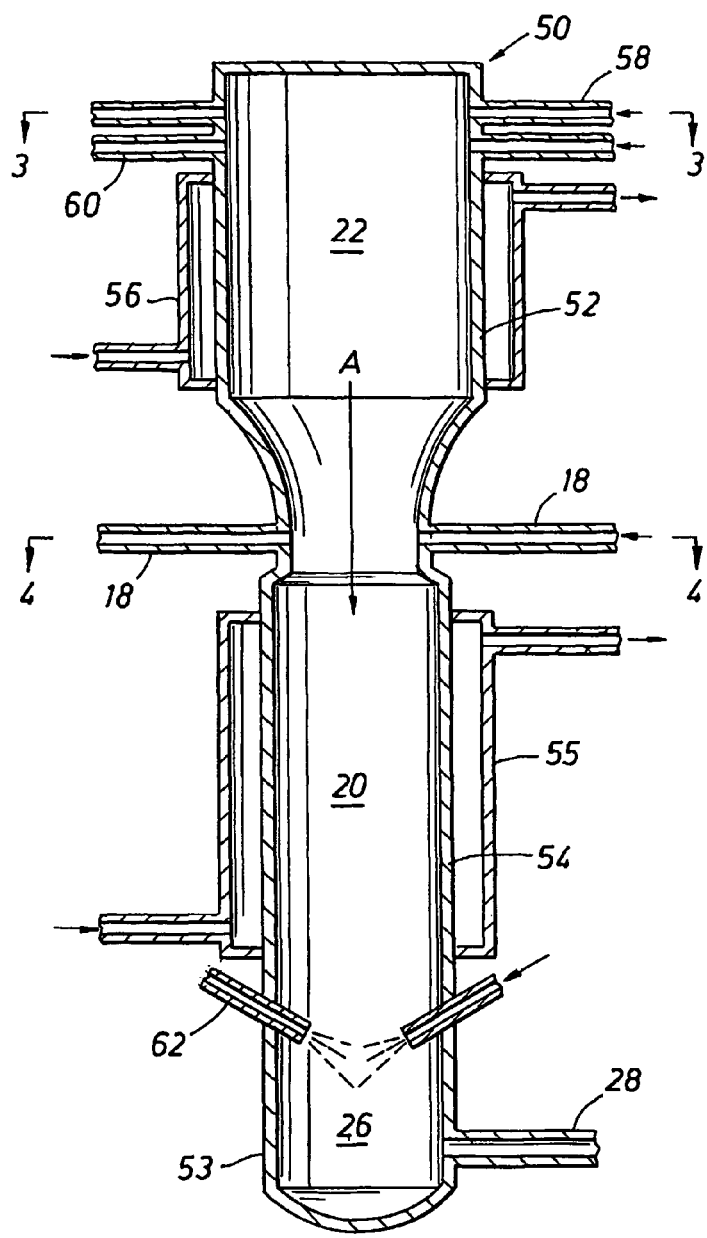
FIG. 2 is a schematic view, in elevation, of an apparatus for effecting conversion of the natural gas to reactive hydrocarbons.

Referring first to FIG. 1, a natural gas feed stream, via line 10, is introduced into first preheater 12 and passes via line 14 to a second preheater 16. The preheated natural gas stream passes via line 18 to a reaction zone 20 where it is admixed with hot gas from hot gas source 22. The hot gas introduced into reaction zone 20 is generally at a temperature of from 1400–3000 K, the temperature of the preheated natural gas entering thermal reaction zone 20 being in the range of from 500–1200 K. Thus, the term "hot gas" as used herein is intended to mean a gas, regardless of its composition which is at a temperature of from 1400–3000 K or, more generally, at a temperature sufficient to effect cracking of methane to produce reactive products or hydrocarbons such as acetylene. In reaction zone 20, there is produced an intermediate product stream of varying composition depending on the nature and source of the hot gas. As described hereafter, if inert or other gasses are used as the hot gas source such inert gasses will be present.

In order to stop the reaction, essentially cracking, in reaction zone 20 and prevent reverse reactions or further reactions which would form coke and other undesirable hydrocarbon compounds, rapid cooling or quenching is essential, generally in a time on the order of 100 milliseconds. This quenching may be achieved by dumping the intermediate product stream into a quench zone, wherein the intermediate product stream is contacted with water or some other quenching agent, e.g., natural gas, liquid products produced by the process, etc. Other quench mediums well known to those skilled in the art can also be employed. The quenched, intermediate product stream passes from quench zone 26 via line 28 to a separator 30 wherein by-products are removed via line 34, hydrogen being removed via line 32. Solids, if present, can also be removed. A stream comprised of reactive hydrocarbons, e.g., wet acetylene, methane, other hydrocarbons and minor amounts of hydrogen is removed from separator 30 via line 36 and introduced into a, preferably low temperature, catalytic liquefaction zone 38 where it is converted to hydrocarbon liquids. Ideally, liquefaction zone 38 produces primarily $C_5+$ isoparaffins and aromatics. However, butane, hexane, heptane and some cyclic compounds are also produced.

If desired, steam may be introduced to the liquefaction zone to achieve the desired conversion results. The preferred reactor conditions in the liquefaction zone are temperatures in the range of from 300–800 K and pressures in the range of from 2–30 bar.

It will be understood that a cooling step and a separation step can be considered as a part of the liquefaction zone 38. Cooling of the product stream produced in liquefaction zone 38 after the reaction has been completed may be necessary, depending upon the method of final separation and the optimum conditions for that separation. If the separation is simply a gas-liquid or final separation, cooling may be necessary. Distillation adsorption or absorption separations processes, including pressure-absorption and membrane separation may be used for the final separation. Any known hydrocarbon liquid-gas separation processes may be used for the final separation step, which, as noted, can be considered a part of liquefaction zone 38. In any event, liquid hydrocarbon produced in liquefaction zone 38 is removed via line 40 for storage or transport. Hydrocarbon gasses separated in the liquefaction zone 38 are recycled via line 42 to the incoming natural gas feed stream 10.

As described above, the cracking or reaction of the natural gas is accomplished by admixing the preheated natural gas stream with a hot gas stream which is at a temperature sufficient to crack the methane in the natural gas to form acetylene and hydrogen albeit that the cracking reaction can also produce ethylene and hydrogen, these cracked hydrocarbon products being considered the "reactive products" or "reactive hydrocarbons" for use downstream in the production of liquid hydrocarbons.

This heating of the natural gas feed stream by the hot gas stream can be accomplished by several preferred techniques. In one technique, the hot gas stream could be generated by the use of electric resistance heaters, direct fired heaters, plasma heaters, screen heaters, shock tubes, adiabatic compression, thermite, photolysis and irradiation, to mention a few. Thus, and by way of example only, a gas, e.g., an inert gas could be introduced via line 44 and multi-position valve 46 through a direct fired heater and heated to the desired predetermined temperature to produce the hot gas stream which would then be introduced into reaction zone 20. When this form of generation of the hot gas stream is employed, the gas to be used can comprise a virtually endless number of gasses including inert gasses, e.g., helium, argon, etc., hydrogen, carbon monoxide, carbon dioxide, water, nitrogen, oxygen, etc. In this regard, it is to be observed that any hydrogen which is separated in separator 30 or recovered from liquefaction zone 38 can pass via line 48 through multi-position valve 46 to be subjected to one of the heating sources or means of heating described above.

Figure 3:
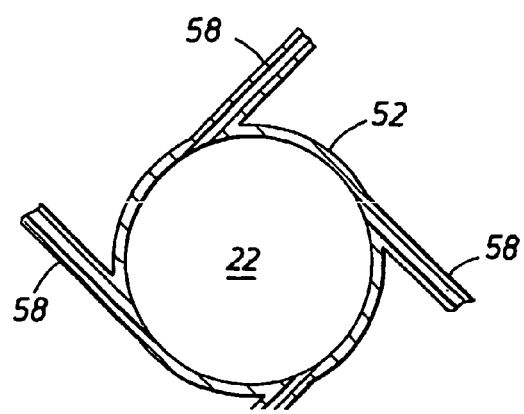
FIG. 3 is a cross sectional view taken along the lines 1—1 of FIG. 3.
Figure 4:
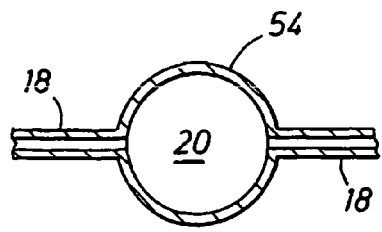
FIG. 4 is a cross sectional view taken along the lines 2—2 of FIG. 3.

An alternative method of providing the hot gas stream is shown in FIGS. 3–5. In this technique, a fuel is burned to produce combustion gasses which form the hot gas stream which are then admixed with the natural gas stream to effect cracking thereof and generate the reactive products discussed above. Referring then to FIG. 3, there is shown a housing 50 which can basically considered as being divided into three portions, i.e., upper portion or combustion chamber 52, essentially forming hot gas source, e.g., source 22 shown in FIG. 1, an intermediate portion 54 essentially forming reaction zone 20 and a lower portion 53 essentially forming quench zone 26. As is conventional, combustion chamber 52 is jacketed with a cooling jacket 56 through which a cooling agent, e.g., water, can be passed. Combustion chamber 52 has a plurality of fuel inlets 58, which as seen FIG. 4, introduce fuel tangentially (or radially if desired) into the combustion chamber 52. There is also a line 60 through which is introduced an oxidizing gas and optionally steam, the oxidizing gas being, for example, an oxygen containing gas, i.e., air, pure oxygen or the like. The fuel can be virtually any combustible material such as natural gas, other hydrocarbons, hydrogen, etc. Indeed, with reference to FIG. 1, recycled hydrogen via line 48 could enter combustion chamber 52 via line 58 together with oxygen or other oxygen containing gas via line 60 and be combusted to form the hot gas. Hydrocarbons which can be employed as fuels can include materials that are normally liquid or solid but can be liquified by heating so as to be injected into the combustion chamber 52. Ideally, the fuels are used in a finally divided form, i.e., an atomized form, if not in the gaseous state. It will also be recognized that mixtures of hydrogen or hydrogen containing gasses, e.g., water gas, can be employed as a fuel and that hydrogen and hydrogen containing gasses in admixture with hydrocarbons can also be employed as the fuel. The fuel and the oxidizing gas are introduced into the combustion chamber 52 at a velocity corresponding to a Mach number of at least 0.8, preferably at sonic speed, which is attained as soon as the ratio of the absolute pressure at which the gasses are introduced into combustion chamber 52 at the entrance to the chamber via line 58, to the absolute pressure in the combustion chamber is about 2:1, through at least one line 58 for the fuel and the oxidizing gas, and then subjected to the combustion process. By mixing and whirling the oxidizing gas and the fuel, a rapid combustion takes place resulting in a flame front that ceases to burn after a very short distance. Accordingly, the combustion chamber 52 can be operated at very high charge rates.

The hot gasses from the combustion and combustion chamber 52 flow at very high velocities in the direction of arrow A into reaction zone 20 (FIG. 1) where they admix with the natural gas feed stream being introduced via line 18. As in the case of the combustion chamber 52, reactor 54 is also provided with a cooling jacket 55 through which a cooling medium such as water can be passed. Additionally, it is preferable that reactor 54 forming reaction zone 20 be lined with a refractory material, e.g., a ceramic or the like.

Because of the high velocity of the combustion gasses entering reaction 20, there is rapid mixing between the natural gas feed stream and the combustion gasses (hot gas stream), and since the combustion gasses are generally at a temperature in the range of 1700–2200 K, the natural gas undergoes a reaction, i.e., cracking, to produce reactive products as described above. The reaction products produced, i.e., the intermediate reaction product stream which exits apparatus 50 via line 28, is first subjected to quench in quench zone 26 with a cooling agent via lines 62 as described above, i.e., a quenching agent such as natural gas, liquid products produced in the process, as well as numerous other cooling or quenching agents well known to those skilled in the art. In effect, the apparatus shown in FIGS. 3, 4 and 5 forms zones 20, 22 and 26 described with respect to FIG. 1. U.S. Pat. Nos. 2,790,838 and 3,047,371, both of which are incorporated herein by reference, for all purposes disclose apparatus which essentially combine zones 20, 22 and 26 into a unitary piece of apparatus.

It will be recognized that when the hot gas comprises combustion gases, it could theoretically be supplied from the hydrogen recovered from separator 30 and liquefactions zone 38, i.e., the hydrogen would form the fuel entering line 58 of apparatus 50 shown in FIG. 3. In such case, there would be no reduced use of natural gas in the entire process other than as the feed stream in line 10.

In cases where a hot combustion gas or flue gas is used as the hot gas, by-products such as water, CO, $CO_2$, etc. will be produced and can be separated in separator 30. Alternatively, if the hot gas comprises, for example, an inert gas which has been heated by a source such as one of the heating sources described above, the inert gas can be separated in separator 30 and recycled to the heating source to again form the hot gas. Also, to the extent solids such as coke or the like are formed in reaction zone 20, they can also be removed in separation zone 30 by techniques well known to those skilled in the art.

A particularly desirable feature of the process of the present invention is that when hydrogen is used as fuel, and the hot gas is generated by combustion of the hydrogen, the natural gas feed stream supplies not only the raw material which is converted into the liquid hydrocarbons but also the fuel for generating the hot gas. Thus, while, as described above, hydrocarbons, e.g., natural gas, can be used as a fuel source, the use of the hydrogen produced in the reaction obviates the necessity for resorting to the use of natural gas or other hydrocarbons as a fuel source.

The foregoing description and examples illustrate selected embodiments of the present invention. In light thereof, variations and modifications will be suggested to one of skill in the art, all of which are in the spirit and purview of this invention.

The invention claimed is:

1. A process for converting natural gas to a hydrocarbon liquid comprising:

providing a stream of natural gas at a selected pressure;

mixing said natural gas stream with a hot gas stream, said hot gas stream being at a temperature sufficient to effect a chemical reaction forming an intermediate product stream containing reactive hydrocarbons, said hot gas stream being heated by being subjected to a heating source without combusting any component of said hot gas stream;

quenching said intermediate product stream; and reacting said quenched intermediate product stream in a catalytic liquefaction zone to produce said hydrocarbon liquid.

2. A process for converting natural gas to a hydrocarbon liquid comprising:

providing a stream of natural gas at a selected pressure;

mixing said natural gas stream with a hot gas stream, said hot gas stream being at a temperature sufficient to effect a chemical reaction forming an intermediate product stream containing reactive hydrocarbons;

said hot gas stream being provided by combusting a fuel with an oxidizing gas to provide combustion gases, said fuel and said oxidizing gas being introduced into a combustion zone at a velocity corresponding to a Mach number of at least 0.8 said fuel and said oxidizing gas being introduced into said combustion zone and combusted in the absence of a firewall, said combustion gases comprising said hot gas stream;

quenching said intermediate product stream; and reacting said quenched intermediate product stream in a catalytic liquefaction zone to produce said hydrocarbon liquid.

3. A process for converting natural gas to a hydrocarbon liquid comprising:

providing a stream of natural gas at a selected pressure;

mixing said natural gas stream with a hot gas stream, said hot gas stream being at a temperature sufficient to effect a chemical reaction forming an intermediate product stream containing reactive hydrocarbons, said hot gas being provided by combusting a fuel with an oxidizing gas in a combustion chamber having an entrance, to provide combustion gases, the ratio of the absolute pressure at which said oxidizing gas and said fuel are introduced into said combustion chamber at said entrance to the absolute pressure in said combustion chamber being about 2:1, said combustion gases comprising said hot gas stream;

quenching said intermediate product stream; and reacting said quenched intermediate product stream in a catalytic liquefaction zone to produce said hydrocarbon liquid.

* * * * *